(12) United States Patent
Cohan et al.

(10) Patent No.: US 7,556,380 B2
(45) Date of Patent: Jul. 7, 2009

(54) APPARATUS AND METHOD FOR SELF-MEASUREMENT OF INTRAOCULAR PRESSURE

(75) Inventors: Bruce E. Cohan, Ann Arbor, MI (US); Andrew C. Pearch, Cumberland, OH (US); Zvi Flanders, Ann Arbor, MI (US); Donald E. Gillespie, Ann Arbor, MI (US)

(73) Assignee: Eyelab Group, LLC, Ann Arbor, MI (US)

( * ) Notice: Subject to any disclaimer, the term of this patent is extended or adjusted under 35 U.S.C. 154(b) by 285 days.

(21) Appl. No.: 10/598,002

(22) PCT Filed: Oct. 20, 2003

(86) PCT No.: PCT/US03/33250

§ 371 (c)(1),
(2), (4) Date: Dec. 14, 2006

(87) PCT Pub. No.: WO2004/036268

PCT Pub. Date: Apr. 29, 2004

(65) Prior Publication Data

US 2008/0021298 A1   Jan. 24, 2008

Related U.S. Application Data

(60) Provisional application No. 60/419,442, filed on Oct. 18, 2002.

(51) Int. Cl.
*A61B 3/02* (2006.01)
*A61B 3/10* (2006.01)

(52) U.S. Cl. .......... 351/222; 351/223; 351/205
(58) Field of Classification Search ........ 351/205, 351/222, 223
See application file for complete search history.

(56) References Cited

U.S. PATENT DOCUMENTS

| 4,951,671 A | 8/1990 | Coan |
| 5,355,884 A | 10/1994 | Bennett |
| 5,830,139 A | 11/1998 | Abreu |

(Continued)

OTHER PUBLICATIONS

Posner A. Home use of the applanometer as an aid in the management of glaucoma. Eye & Ear Nose Throat Mon 1965; 44:64-66.

(Continued)

*Primary Examiner*—Jordan M. Schwartz
*Assistant Examiner*—James C Jones
(74) *Attorney, Agent, or Firm*—Brooks Kushman P.C.

(57) ABSTRACT

An apparatus and method for the self-measurement of intraocular pressure utilize a tonometer disposed within a housing and having a tonometer tip. The apparatus further includes an adjustment mechanism in communication with the tonometer for positioning the tonometer tip in contact with a test eye of the user, and an illuminator mounted within the housing adjacent the tonometer tip. A receiver is aligned with the tonometer tip for receiving an applanation pattern created by contact of the tonometer tip with the test eye, and a display is provided in communication with the receiver for displaying the applanation pattern to an observing eye of the user. The intraocular pressure of the test eye is determined from a force applied by the tonometer tip upon observation of a selected applanation pattern by the observing eye.

27 Claims, 8 Drawing Sheets

U.S. PATENT DOCUMENTS

| | | |
|---|---|---|
| 6,440,070 B2 | 8/2002 | Israel |
| 6,981,946 B2 * | 1/2006 | Davidson .................... 600/405 |
| 2004/0002640 A1 | 1/2004 | Luce |

OTHER PUBLICATIONS

Jensen AD, Maumenee AE. Home tonometry. Am J Ophthalmol 1976; 76:929-932.

Alpar J. The use of home tonometry in the diagnosis and treatment of glaucoma. Glaucoma 1983; 5:130-32.

Zeimer RC, Wilensky JT. An instrument for self-measurement of intraocular pressure. IEEE Trans Biomed Eng 1982; 29:178-183.

Groenhoff S, Draeger J, Ceutsch C, Wiezorrek R, Hock B. Self-tonometry; technical aspects of calibration and clinical application. Int Ophthalmol 1992; 16:299-303.

Kupin TH, Shin DH, Juzych MS, Olivier MMG, Kim C. Use of a Tono-Pen for long term home tonometry. Am J Ophthalmol 1993; 116:643-644.

As Glaucoma Treatment Advances, Vision is Saved. The New York Times. Dec. 25, 2001.

Stewart WC, Cascairo MA, Banta R. The use of a new portable noncontact tonometer in home tonometry. Ann Ophthalmol 1991; 23:377-382.

Carenini BB, Brogliatti B, Tonetto C, Renis E. The Pulsair-Keeler non-contact tonometer in self-tonometry: preliminary results. Int Ophthalmol 1992; 16:295-297.

* cited by examiner

APPARATUS AND METHOD FOR SELF-MEASUREMENT OF INTRAOCULAR PRESSURE

CROSS-REFERENCE TO RELATED APPLICATIONS

This application claims the benefit of U.S. provisional application Ser. No. 60/419,442 filed Oct. 18, 2002.

BACKGROUND OF THE INVENTION

1. Field of the Invention

This invention relates to an apparatus and method for the self-measurement of intraocular pressure.

2. Background Art

Intraocular pressure (IOP) is a physiological parameter routinely measured by eye care professionals. Elevated IOP is the most important risk factor in primary open angle glaucoma (POAG) which, combined with normal tension glaucoma (NTG), is the second leading cause of irreversible blindness in the United States. Patients with POAG and NTG have the same characteristic optic neuropathy (cupping) and visual field loss, but in NTG the IOPs have never been found to be elevated. Elevated IOP is also found in patients with ocular hypertension (OHT), but not the neuropathy or field changes. The only current treatment for POAG, NTG and OHT is reduction of IOP.

The instrument that is the reference standard for IOP measurement is the Goldmann applanation tonometer, used worldwide by opthalmologists for over 40 years. This instrument functions to flatten part of the cornea to measure eye pressure, wherein the pressure within the eye is determined by how much force is needed to flatten the cornea.

Glaucoma management, which is so dependent on IOP, would benefit greatly by the acquisition of more IOP data. Essentially all IOP measurements are obtained on visits to the opthalmologist's office—usually one measurement during typical office hours, and rarely more than one visit every two or three months. In glaucoma management, there is no parallel to the ubiquitous monitoring by diabetic patients of capillary blood glucose or by arterial hypertensive patients of blood pressure and heart rate. For these conditions, adjuncts in patient care increase the volume of measurements during clinic hours as well as extend the monitoring beyond the eight hours that the clinic is open.

Measurement of IOP at different times of the day usually yields different readings, sometimes highest at night. However, there is considerable variability in the diurnal pattern between individuals. Differences in IOP throughout the day are of special interest. In some POAG patients, despite treatment which results in normal IOPs (measured in the opthalmologist's office), cupping and field loss can progress. In NTG, cupping occurs and can progress in the presence of IOP within the normal statistical limits (measured in the opthalmologist's office). In OHT, over time, cupping and field loss can develop. The question in these cases is whether the progression (in POAG and NTG) and development (in OHT) of glaucoma damage is due to elevated IOP at times of the day when they cannot be measured in the opthalmologist's office.

The answer is a clinical test with a long history, the diurnal IOP curve, which involves measuring a patient's IOP a number of times throughout a 24 hour period. In "Emerging Perspectives in Glaucoma: Optimizing 24-hour Control of Intraocular Pressure" (*Am J Ophthalmol* 2002, 133: S1-S10), Wax et al. summarize the importance of 24-hour control of IOP in the management of POAG and NTG to prevent patients from progressing to blindness (see also Oliver et al., *Am J Ophthalmol* 2002, 133: 764-772). Perhaps in OHT, in which standard medication protocols reduce the incidence of progression to cupping and visual field loss, an additional risk predictive factor might be uncovered in this inhomogeneous group by expanding the scope of IOP testing from an 8- to a 24-hour day.

However, the diurnal IOP curve is a problematic test because it typically involves admitting the patient to a hospital or sleep laboratory where a resident or technician measures IOP at intervals throughout the day and night. It seems likely that results of diurnal curves might be affected by the inherently more stressful institutional setting, sleeping in an unfamiliar bed in a strange hospital room or sleep laboratory, and being awakened multiple times during the night by someone who measures the patient's IOP. In one systematic study of diurnal IOP using the Goldmann tonometer (see Hayreh et al., *Am J Opthalmol* 1994, 117: 603-624), the earliest measurement was at 7 am and the latest was at 10 pm. Another study reported Goldmann readings throughout the night, sitting and "10 meters" from the patient's room (see Ido et al., *Opthalmol* 1991, 98: 296-300). This study showed that frequent awakening of the patient in a hospital for the measurement can be a confounding factor, and so the research design was altered to awaken the patient once at night at a random time. Therefore, obtaining a full diurnal curve with this protocol would require the patient to be admitted to the hospital or a sleep laboratory four to five different nights, ideally with a slit lamp with a Goldmann tonometer in the patient's room to measure IOP immediately upon awakening while in the lying position. Of course, this is not possible economically and logistically for in-patient care or screening. In reality, diurnal IOP curves are currently not generally part of the standard of care in glaucoma management, except in clinical research centers. When diurnal curves are obtained, data are typically limited to several points during a single, likely uncomfortable, night.

In obtaining diurnal IOP curves, the tonometric method is an important, but not a simple, consideration. Because of the complicated logistics, this test has often been done without using the Goldmann applanation tonometer. For example, recently, Liu et al. reported that the lying position is a factor in the increase in IOP in some patients, although the nighttime values in the lying position were not compared with sitting nighttime IOP measurements (*Invest Opthalmol Vis Sci* 1999, 40: 2912-2917). This extensive study was based on measurements made with a pneumotonometer, which has been shown to correlate well with the Goldmann applanation tonometer (see Quigley and Langham, *Am J Opthalmol* 1975, 80: 266-273). However, the pneumotonometer is an instrument on which opthalmologists do not base their clinical decisions.

The effect of a subject's body position on IOP has been the source of much debate in the literature. Of the many daytime studies, most using the Goldmann tonometer, most have shown a 1-4 mm Hg higher pressure in the lying position (see Tsukahara and Sasaki, *Br J Opthalmol* 1984, 68: 389-392; Yamabayashi et al., *Br J Opthalmol* 1991, 75: 652-655; Anderson and Grant, *Invest Opthalmol* 1973, 12: 204-212), some a larger difference (see Leonard et al., *Br J Opthalmol* 1983, 67: 362-366), and some no difference at all (Frampton et al., *Am J Optom Physiol Opt* 1987, 64: 54-61; Strobl and Follman, *Ophthalnologica* 1962, 144: 57-61; Kindler-Loosli et al., *Albrecht v. Graefes Arch klin exp Opthalmol* 1975, 194: 17-21). There has been no study of nighttime Goldmann IOP in patients in the lying position. In addition to position, other factors have been reported to influence a patient's IOP throughout the night, including the light that a patient's eyes receive (see Frampton et al.), the blood melatonin level (see Willdosoet et al., *Ophthal Physiol Opt* 1993, 13: 357-365), a blood pressure change associated with waking (see Zeimer et al., *Opthalmol* 1990, 97: 547-550), the fact that the patient has or has not slept (see Frampton et al.; Brown et al., *Ophthal Physiol Opt* 1988, 8: 246-248; Brown et al., *Ophthal Physiol Opt* 1988, 8: 249-252), and the actual state of sleep the subject was in when awakened (see Noel et al., *Opthalmol* 2001, 108: 139-144). This body of research makes it seem unlikely that a higher IOP at night, when it occurs, is due entirely to position.

The disadvantages for both patients and medical personnel of an institutional site in measuring diurnal IOP led to the idea of home tonometry, which Posner noted in 1965, having patients use a Maklakoff type tonometer (*Eye & Ear Nose Throat Mon* 1965, 44: 64-66). Jensen and Maumenee (*Am J Opthalmol* 1976, 76: 929-932) and later Alpar (*Glaucoma* 1983, 5: 130-132) had a family member measure the patient's IOP with the Schiotz tonometer.

A more recent approach to measuring diurnal IOP in the home environment introduced the concept of self-tonometry. Two technically sophisticated instruments, both hand-held and based on the applanation principle of the Goldmann tonometer, have been studied. In Zeimer and Wilenski's instrument (*IEEE Trans Biomed Eng* 1982, 29: 178-183), the IOP endpoint is detected by a photodiode array optical device instead of the signature pattern recognition used in Goldmann tonometry. Draeger and group used a microprocessor controlled optical sensor (see Groenhoff et al., *Int Opthalmol* 1992, 16: 299-303). Both showed promise in the hands of their inventors, but others have found the correlation of patient measurements and ophthalmologist measurements using the Goldmann tonometer problematic, and also found that these devices can be moderately difficult to use. What may be most significant is the limited interest in these instruments since their invention in the 1980's, despite the concurrent heightened awareness of the potential importance of diurnal IOP.

As would be expected, self-tonometry with non-contact tonometers (see Stewart et al., *Ann Opthalmol* 1991, 23: 177-182; Carenini et al., *Int Opthalmol* 1992, 16: 295-297) that have been shown to be less reliable than the Goldmann method in the hands of opthalmologists has met with a general lack of professional interest. Finally, the Tono-Pen®, based on the McKay-Marg applanation principle, is used by some opthalmologists' technicians for IOP screening. While it has occasionally been used for self-tonometry (see Kupin et al., *Am J Ophthalmol* 1993, 116: 643-644), it is not easy to apply to oneself, and an ophthalmologist would not depend on measurements with a screening instrument as a basis for clinical decisions.

SUMMARY OF THE INVENTION

Therefore, it is an object according to the present invention to provide an apparatus and method for self-measurement of intraocular pressure which allow a user to easily obtain reliable measurements of intraocular pressure on herself/himself.

It is a further object according to the present invention to provide an apparatus and method for self-measurement of intraocular pressure which facilitate more frequent measurements of intraocular pressure than are possible in a clinical setting.

Accordingly, an apparatus for the self-measurement of intraocular pressure by a user is provided which includes a housing and a tonometer disposed within the housing and having a tonometer tip. The apparatus further includes an adjustment mechanism in communication with the tonometer for positioning the tonometer tip in contact with a test eye of the user, and an illuminator mounted within the housing adjacent the tonometer tip. A receiver is aligned with the tonometer tip for receiving an applanation pattern created by contact of the tonometer tip with the test eye, and a display is provided in communication with the receiver for displaying the applanation pattern to an observing eye of the user. The intraocular pressure of the test eye is determined from a force applied by the tonometer tip upon observation of a selected applanation pattern by the observing eye.

In one embodiment, the receiver includes a video camera, and the display includes at least one video monitor. In another embodiment, the receiver includes a beam splitting mirror, and the display includes a display mirror aligned with the beam splitting mirror. The housing can include a base, a guide plate movably positionable with respect to the base, and a support extending upwardly from the guide plate, where the support has the tonometer, receiver, and display mounted thereon. A chin-forehead rest is preferably attached to the base, and a pair of lens holders can be mounted to the housing for receiving corrective lenses. Alternatively, the housing can be arranged to be hand-held and include first and second ocular portions, where the tonometer tip and receiver are disposed within the first ocular portion and the display is disposed within the second ocular portion. In either embodiment, a video recorder can be provided in communication with the receiver. Preferably, the selected applanation pattern is an applanation endpoint pattern.

In further accordance with the present invention, a hand-held apparatus for the self-measurement of intraocular pressure by a user is provided including a housing having a first ocular portion and a second ocular portion, and a tonometer disposed at least partially within the first ocular portion and having a tonometer tip. An adjustment mechanism in communication with the tonometer for positioning the tonometer tip in contact with a test eye of the user, and an illuminator is mounted within the housing adjacent the tonometer tip. A receiver is disposed within the first ocular portion and aligned with the tonometer tip for receiving an applanation pattern created by contact of the tonometer tip with the test eye. A display is disposed in the second ocular portion and in communication with the receiver for displaying the applanation pattern to an observing eye of the user, where the intraocular pressure of the test eye is determined from a force applied by the tonometer tip upon observation of a selected applanation pattern by the observing eye.

In one embodiment, the receiver includes a video camera, and the display includes at least one video monitor. In another embodiment, the receiver includes a beam splitting mirror, and the display includes a display mirror aligned with the beam splitting mirror. In this latter embodiment, the apparatus preferably further includes at least one focusing lens disposed within the housing and aligned with the display mirror for focusing the applanation pattern for the observing eye. In either embodiment, an LCD display is preferably provided for displaying the intraocular pressure reading. Preferably, the selected applanation pattern is an applanation endpoint pattern.

In a preferred embodiment, the tonometer includes a force applicator for actuating movement of the tonometer tip to apply a force to the test eye, a strain gauge in communication with the force applicator for sensing an applied force, and a microprocessor in communication with the strain gauge for controlling the applied force and determining the intraocular pressure from the applied force.

In a reversible configuration of the apparatus, a first adjustment mechanism is provided on a top surface of the housing and a second adjustment mechanism is provided on a bottom surface of the housing such that the housing is operable in a first orientation and in a second orientation rotated 180° about its longitudinal axis. The housing further includes an aperture arranged to receive a member for activating one of the first and second adjustment mechanisms depending upon the orientation of the housing. In another reversible configuration, the apparatus includes a plate having a first connector provided on a bottom surface thereof and the adjustment mechanism provided on a top surface thereof. The housing includes a second connector on both a top and bottom surface thereof arranged to mate with the first connector such that the housing is operable in a first orientation and in a second orientation rotated 180° about its longitudinal axis.

Correspondingly, a method for the self-measurement of intraocular pressure by a user includes providing a housing having a tonometer disposed therein, the tonometer having a tonometer tip, placing a test eye and an observing eye of the user adjacent to the housing. The method further includes illuminating the test eye, and positioning the tonometer tip in contact with the test eye. Still further, the method includes receiving an applanation pattern created by contact of the tonometer tip with the test eye, displaying the applanation pattern to the observing eye, and determining the intraocular pressure of the test eye based on the force applied by the tonometer tip upon observation of a selected applanation pattern by the observing eye.

The applanation pattern can be received by a beam splitting mirror and displayed using a display mirror, or alternatively the applanation pattern can be received with a video camera and displayed using at least one video monitor. The method further includes instilling dye and anesthetic substances in the test eye, and rotating the housing 180° about its longitudinal axis to obtain a measurement of intraocular pressure for another test eye.

The above objects and other objects, features, and advantages of the present invention are readily apparent from the following detailed description of the best mode for carrying out the invention when taken in connection with the accompanying drawings.

DETAILED DESCRIPTION OF THE PREFERRED EMBODIMENT(S)

Figure 1:
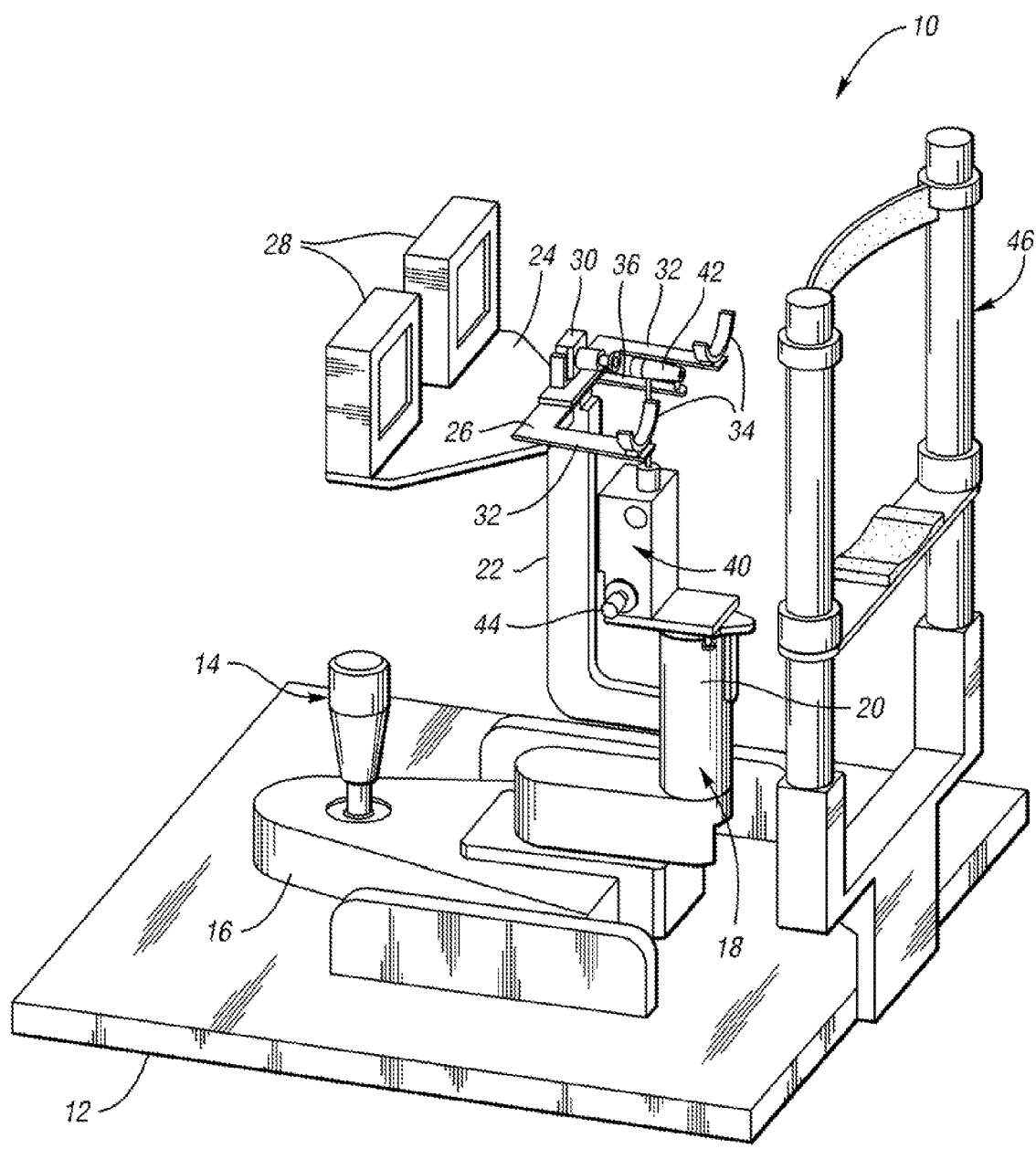
FIG. 1 is a perspective view of a self-tonometry apparatus according to the present invention.
Figure 2:
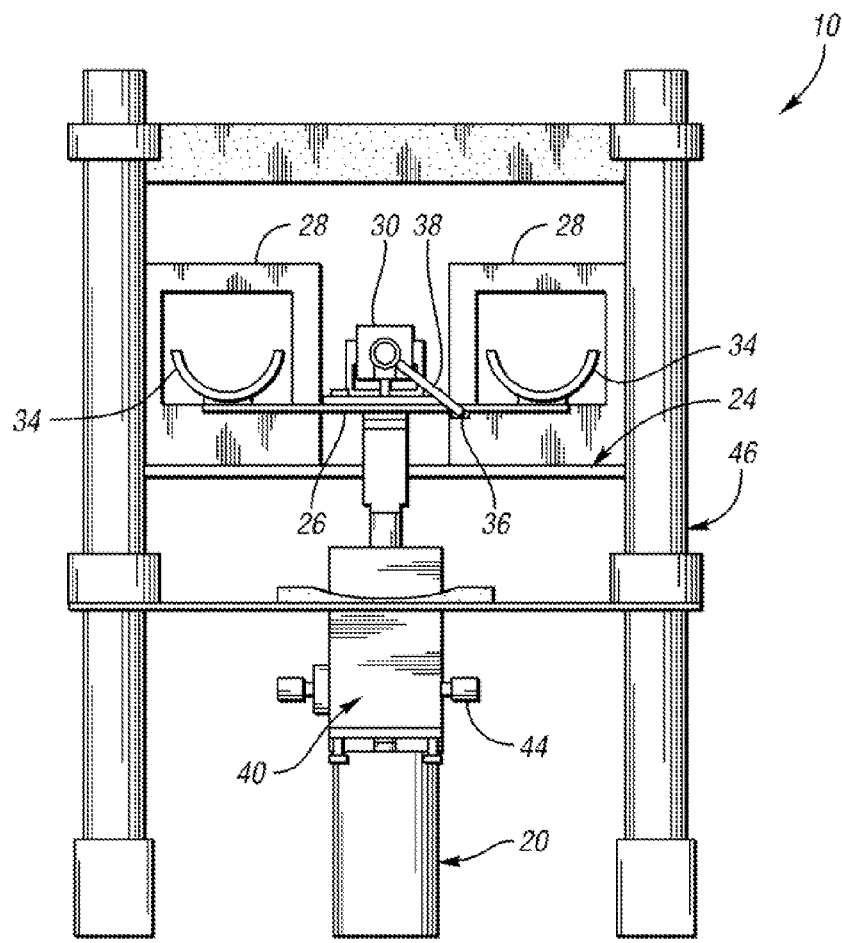
FIG. 2 is a fragmentary, end elevational view of the self-tonometry apparatus of FIG. 1.

The present invention is directed to a apparatus and method for self-measurement of intraocular pressure (IOP). Referring first to FIGS. 1 and 2, a first embodiment of a self-tonometry apparatus 10 according to the present invention is illustrated. Apparatus 10 somewhat resembles a conventional slit lamp (Haag-Streit or the like) except that the microscope and illumination tower of the slit lamp are replaced with illumination and imaging components according to the present invention. Apparatus 10 comprises a housing which includes a base 12 with a joystick 14 and guide plate 16 disposed thereon, similar to a conventional slit lamp. Joystick 14 allows movement of guide plate 16 relative to base 12 in left and right directions, and toward and away from the user. The user can also turn the joystick 14 in a clockwise manner and in a counterclockwise manner to move guide plate 16 up and down. As best shown in FIG. 1, the housing further includes a support 18 extends upwardly from guide plate 16 and includes a first post 20 for mounting a tonometer 40 and a second post 22 having mounting plates 24, 26 for mounting the various illumination and imaging components described below.

With continuing reference to FIGS. 1 and 2, mounting plate 24 is arranged to hold at least one display, preferably two spaced LCD color video monitors 28 (for example, 2.5" screen, Casio EV-570, Casio, Denver, Colo.; or 2.9" screen, 4.7 oz., 80×91×27 mm, Citizen M329 Mark II, CBM America Corporation, Torrance, Calif.; or 18 mm diagonal, 800×600 pixel, CRL Opto Limited). Mounting plate 26 is arranged to receive an ultra-miniature color video camera 30 (for example, Canon PowerShot S40, Canon, Lake Success, N.Y.; 1.3 oz, 25×25 mm, Defender Security; or 3.6 mm lens; Sony ¼" CCD; horizontal resolution more than 380 TV lines), which receives the applanation pattern and provides video output to monitors 28, preferably with approximately a 10× magnification. Mounting plate 26 also includes first arms 32 which are provided with loose lens holders 34 (for example, Humphrey-Zeiss, Dublin, Calif.) attached thereto for receiving corrective lenses, both for refractive errors and presbyopia, if desired to accommodate the approximately 6 inch distance between a user's eye and video monitors 28. Mounting plate 26 also includes a second arm 36 arranged to hold an illuminator 38, typically a blue LED. A tonometer 40, preferably a standard Goldmann applanation tonometer (16.9 oz), having a tonometer tip 42 and tonometer dial 44 is attached to first post 20 in alignment with video camera 30 in order to image the applanation pattern as described below. As best shown in FIG. 2, illuminator 38 is placed adjacent to tonometer tip 42, wherein the angle of illuminator 38 shown herein is merely exemplary. A chin-forehead rest 46 is also attached to base 12 as in a conventional slit lamp.

The wiring for each component described above preferably runs to a single cable connector and then to a power supply (not shown), wherein the wiring is preferably minimized and the transformers simplified for home use. Apparatus 10 according to the present invention is preferably designed for portability in that it is light, compact and easy to use in a user's home environment. Lightweight materials, such as aluminum and plastics, can be used to construct base 12, joystick 14 and guide plate 16, support 18, and chin-forehead rest 46, and compactness can be achieved with telescoping vertical supports of chin/forehead rest 46. Apparatus 10 can be used with ease for testing the IOP of either the left or right eye as described more fully below.

Figure 3:
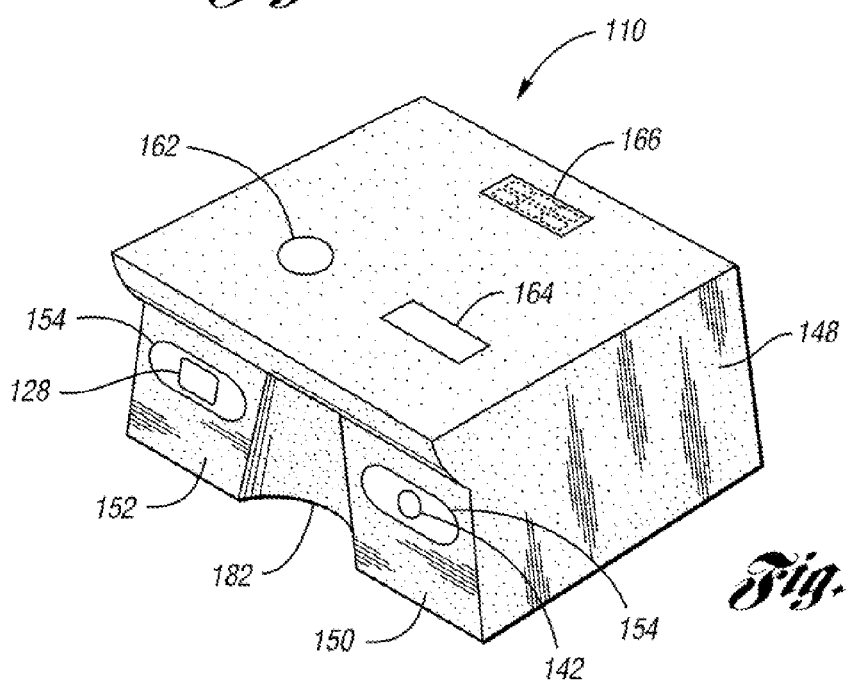
FIG. 3 is a perspective view of a hand-held self-tonometry apparatus according to the present invention.

An alternative embodiment of the self-tonometry apparatus 110 according to the present invention is depicted in FIGS. 3-8 and, where applicable, the reference numerals correspond to those for apparatus 10 except for the addition of a "1" prefix. In this embodiment, apparatus 110 is configured to be hand-held by the user similar to binoculars and rested on the brow similar to the Perkins version of the Goldmann applanation tonometer. With reference to FIG. 3, apparatus 110 includes a housing 148 having a first ocular portion 150 and a second ocular portion 152. Each ocular portion 150, 152 includes an eye aperture 154 sized for viewing therethrough by either the test eye or observing eye of the user. Housing 148 also preferably includes an indentation 182 to accommodate a user's nose for ease of use. An on/off button 162, an adjustment mechanism such as control lever 164 or the like for adjusting the position (i.e., pressure) of the tonometer tip 142, and LCD display 166 for displaying the IOP reading are preferably provided on a top surface of housing 148 as shown. Apparatus 110 is preferably constructed from lightweight materials such as aluminum or plastics and is designed to be compact in size. While tonometer tip 142 depicted herein is similar to that of a Goldmann applanation tonometer, it is understood that a tonometer tip of different shape or dimension can alternatively be utilized in accordance with the present invention.

Figure 4:
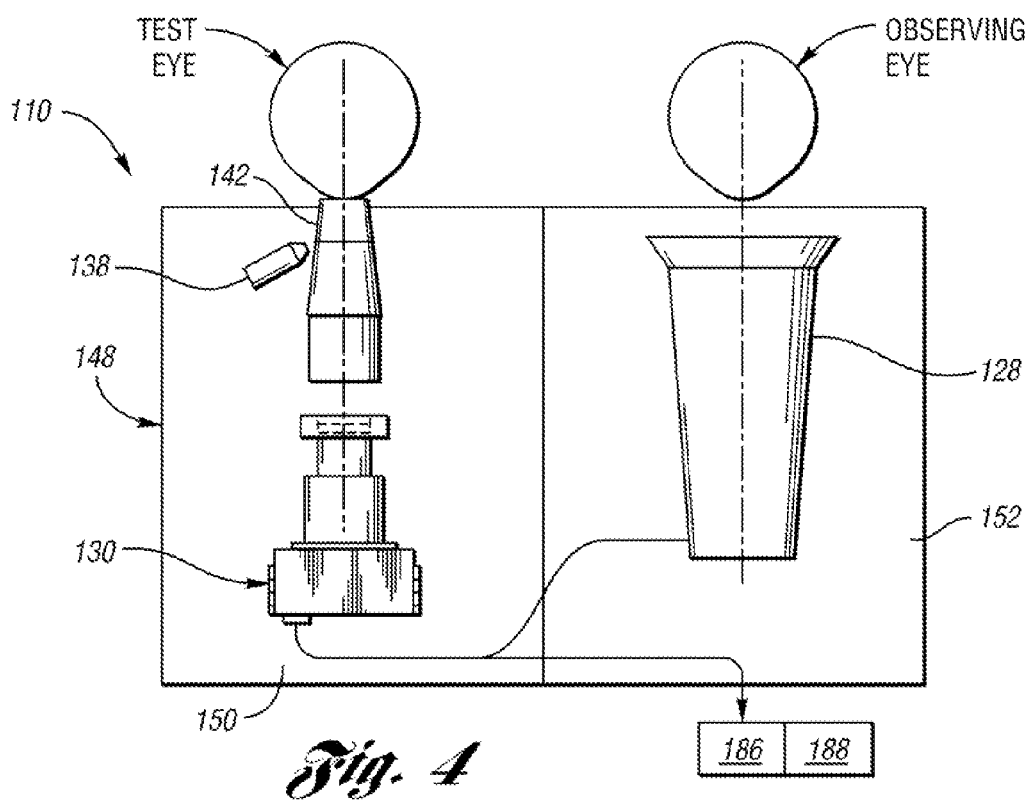
FIG. 4 is a schematic illustration of several components of a first embodiment of the hand-held apparatus of FIG. 3.

Referring now to FIG. 4, one embodiment of apparatus 110 includes a video camera 130, tonometer tip 142 and illuminator 138 mounted in first ocular portion 150, and a video monitor 128 with corrective optics mounted in second ocular portion 152. In an alternative embodiment depicted in FIG. 5, a classical optical train is substituted for video camera 130 and video monitor 128, including a display mirror 156 and at least one focusing lens 158 mounted in first ocular portion 150 and a beam splitting mirror 160 mounted in second ocular portion 152. As shown, beam splitting mirror 160 is aligned with tonometer tip 142 and functions to deflect the applanation pattern image to display mirror 156 for viewing by the user as well as to transmit the applanation pattern image to a video monitor 186 and/or video recorder 188 for optional external monitoring as described below. Of course, it is fully contemplated that the configuration of FIG. 5 could also be utilized in the apparatus 10 described with reference to FIGS. 1 and 2.

Figure 5:
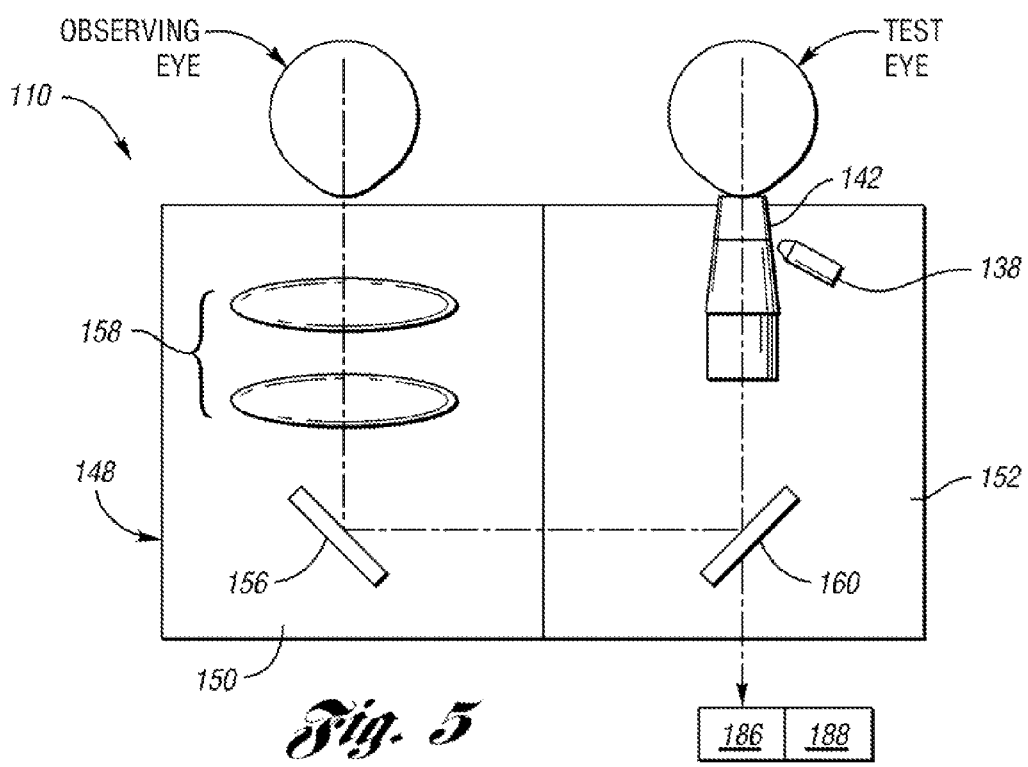
FIG. 5 is a schematic illustration of several components of a second embodiment of the hand-held apparatus of FIG. 3.
Figure 6:
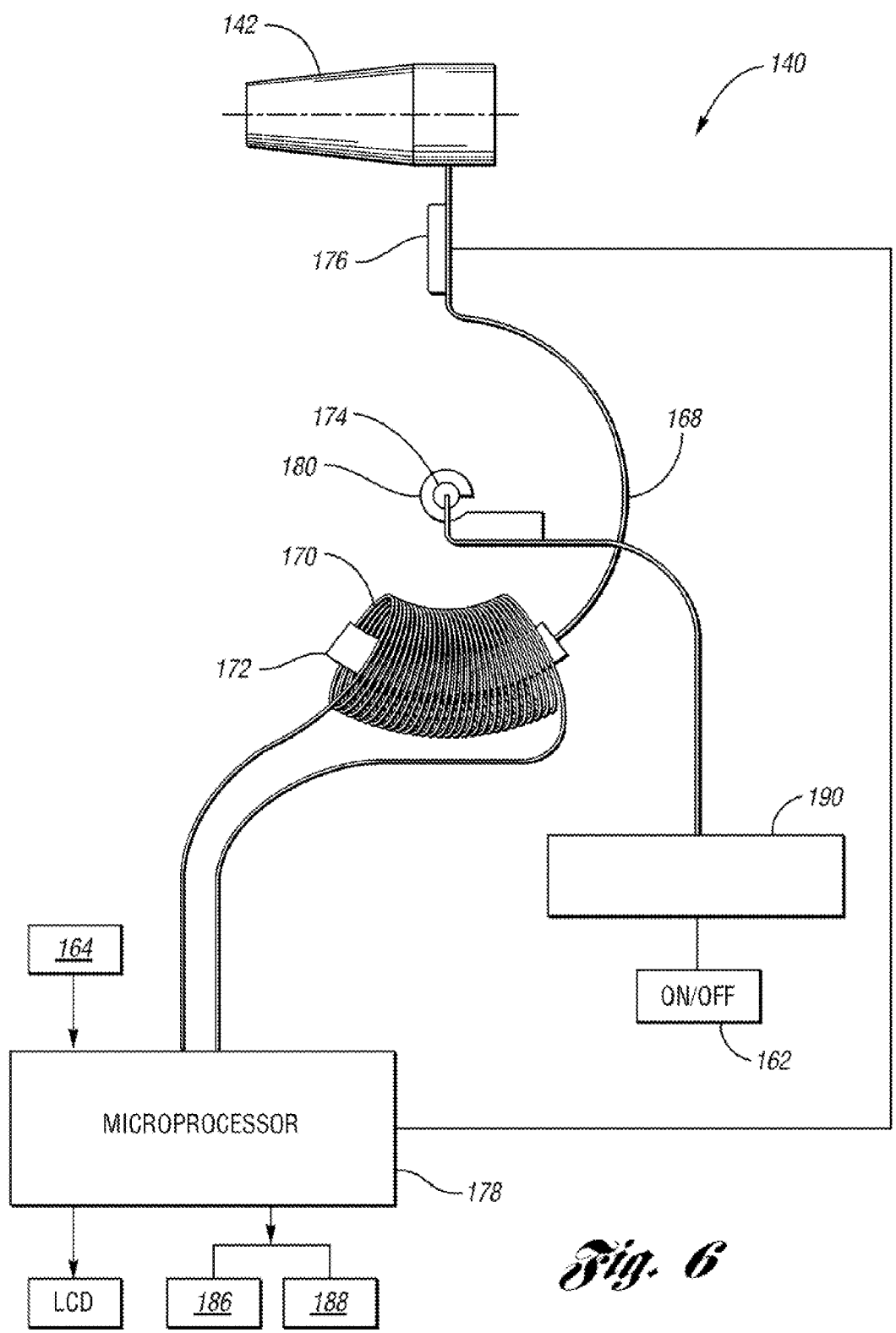
FIG. 6 is a schematic illustration of a modified tonometer and associated components for the hand-held apparatus of FIG. 3.

With reference now to FIG. 6, a modified, more compact tonometer 140 is preferably utilized in conjunction with apparatus 110 depicted in FIGS. 3-5. A force applicator, such as a rotary voice coil 168 (for example, 1.8 in wide×1.2 in long, BEI Technologies, Inc.), is connected to tonometer tip 142 and actuates movement of tonometer tip 142 for applying a controlled applanating load to the cornea, where a current coil 170 and magnetic core 172 provide movement about a pivot 174. With current in the rotary coil 168, the magnetic core 172 advances the tonometer tip 142 toward the test eye. A strain gauge 176 senses the applanating load applied to the cornea, and a microprocessor 178 in communication with the strain gauge 176 and tonometer control lever 164 controls this load and provides signal processing to give the IOP reading. The tonometer tip 142 is poised by counterbalancing mass around the pivot 174, thus neutralizing the effect of gravity in measurements made sitting and lying, and also in microgravity environments. A coiled spring 180 maintains the at rest position of the tonometer tip 142 with respect to housing 150. On/off button 162 controls the supply of power to tonometer positioning slide 190 and illuminator (see FIGS. 4-5). The applanating load is preferably limited to the applanation standard 8 grams by microprocessor control of maximum current to the current coil 170. As an alternative to rotary voice coil 168, other force application devices could include a linear voice coil, bimetallic elements, NITINOL memory alloys, parallel differential motion of near members (to amplify movement), thermal-activated bellows, and bimorphic elements, among others. Of course, a standard Goldmann applanation tonometer 40 or another tonometer could alternatively be utilized and housing 148 modified accordingly.

Given that tonometer tip 142 is disposed in only one of first or second ocular portions 150, 152, apparatus 110 is configured for testing one eye and then must be rotated 180° about its longitudinal axis in order to test the other eye. However, ideally a user should be able to control the positioning of the tonometer tip 142 for both eyes with the same hand to maintain consistency. Accordingly, with reference now to FIG. 7, housing 148 could include a centrally located, keyed aperture 192 arranged to receive an elongated rod 194 or the like. Rod 194 includes a nose/forehead brace 184 attached to one end thereof, and includes a tab 196 disposed along the rod 194 as shown. Control lever 164, and preferably also on/off button 162 and LCD display 166, are provided on both the top and bottom surfaces of housing 148, wherein only one set of controls 162, 164, 166 is activated at any particular time.

Figure 7:
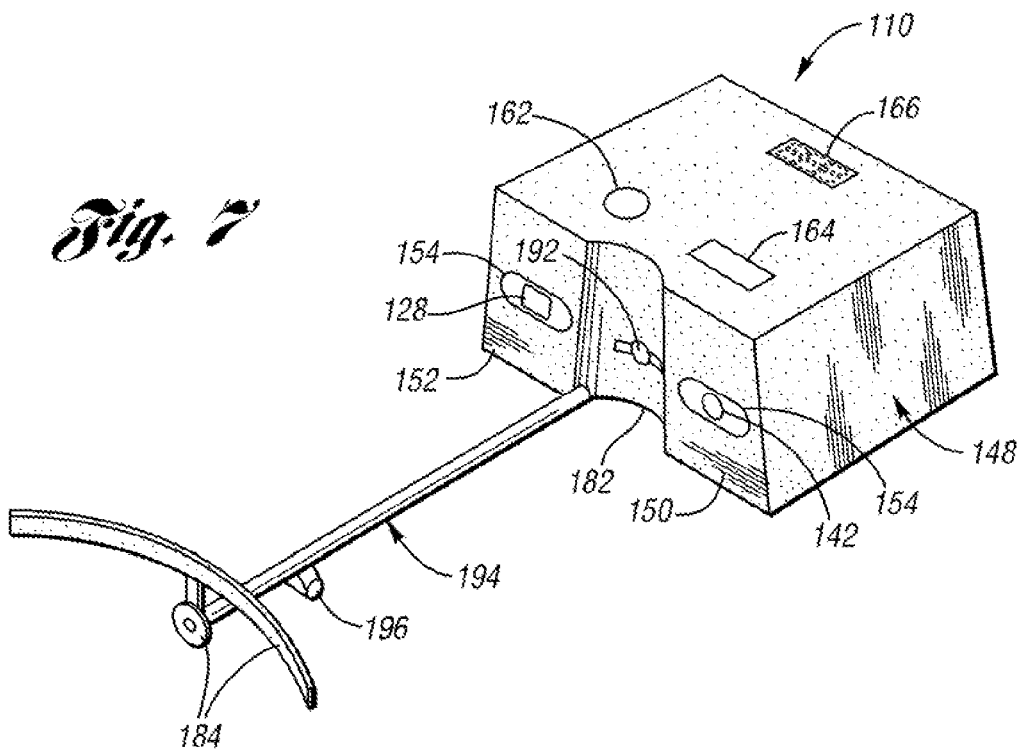
FIG. 7 is a perspective view of a reversible configuration of the hand-held apparatus of FIG. 3.

With continuing reference to FIG. 7, when rod 194 is inserted into aperture 192, the location of tab 196 activates an internal switch (not shown) to indicate the orientation of housing 148, and the controls 162, 164, 166 on the appropriate side of housing 148 are activated. To use apparatus 110 for the other eye, rod 194 is simply removed from aperture 192, housing 148 is rotated 180° about its longitudinal axis, and rod 194 is replaced in aperture 192, thus triggering activation of the opposite set of controls 162, 164, 166. As an additional benefit, the mating of aperture 192 and tab 196 serves to ensure that rod 194 and attached nose/forehead brace 184 are properly aligned within a horizontal plane for the user. Alternatively, an external switch (not shown) could be provided to activate the appropriate controls 162, 164, 166 depending upon the orientation of housing 148.

Figure 8:
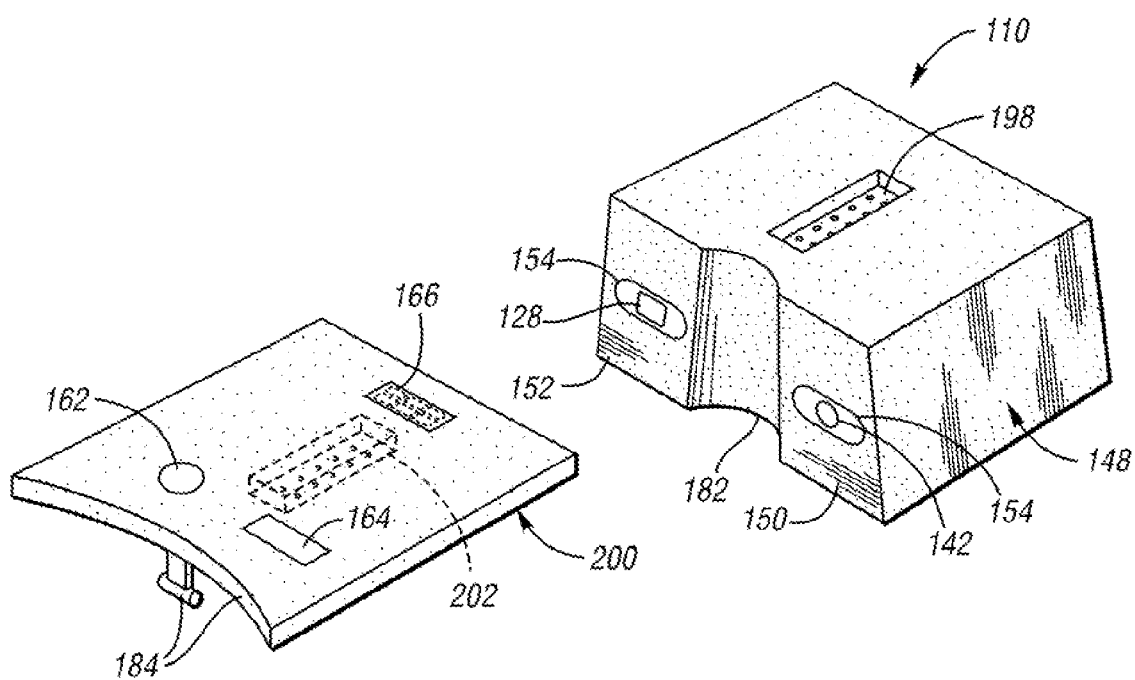
FIG. 8 is a perspective view of another reversible configuration of the hand-held apparatus of FIG. 3.

In the alternative embodiment depicted in FIG. 8, housing 148 is constructed with a first connector, such as receptacle 198, provided on both the top and bottom surfaces thereof. A plate 200 or the like is provided having a second connector, such as plug 202, disposed on an underside thereof and arranged to mate with receptacles 198. Plate 200 further includes on/off button 162, control lever 164, and LCD display 166, as well as nose/forehead brace 184. In operation, housing 148 is connected to the underside of plate 200 via the mating of plug 202 and receptacle 198 for testing a first eye. After testing of the first eye is completed, housing 148 and plate 200 are disengaged, housing 148 is rotated 180° about its longitudinal axis, and receptacle 198 on the opposite side of housing 148 is engaged with plug 202 for testing of the second eye. Of course, plugs 202 could be provided on housing 148 and receptacle 198 could be provided on plate 200. As still another alternative, two different configurations of apparatus 110 (FIG. 3) could be provided as a kit, one with tonometer tip 142 in the first ocular portion 152 for testing one eye, and one with tonometer tip 142 in the second ocular portion 154 for testing the other eye.

For either apparatus 10 or 110, the adjustment of tonometer tip 142 could be automated to obtain the endpoint applanation pattern. Proximity devices could be used to detect the presence of the eye as the tonometer tip 42, 142 is applied to the cornea. Once the tip 42, 142 is in contact with the cornea, image recognition software could use stepper motors to move the tonometer 40, 140 through its 3-axes of movement (up and down, right and left, toward and away) until the applanation pattern is centered and the endpoint pattern is reached.

Additionally, for either apparatus 10 or 110, external monitoring can be accomplished by viewing output from video camera 30, 130 on an additional video monitor 186. The applanation pattern image being viewed by the user can then be simultaneously viewed by the physician, and is helpful for teaching users how to use the apparatus 10, 110. Self-tonometry data can also be recorded to provide a direct, valid, verifiable, highly dependable assessment of the reliability of use of the apparatus 10, 110 at home. A video recorder 188 can be provided in communication with the video camera 30, 130, and the output of microprocessor 178 analyzed to provide the applanation pattern images and the IOP readings, respectively, for subsequent assessment of the applanation endpoint patterns users obtain at home. The recording could be activated by the user's pressure on sensors (not shown) provided in the chin-forehead rest 46 or ocular portions 152, 154. Data recording during self-tonometry could include the day, time, a still image of the applanation endpoint pattern, and the IOP.

Prior to initiating testing using either apparatus 10 or 110 described above, dye (for example, fluorescein) and anesthetic (for example, benoxinate, Fluorox, Ocusoft, Inc.) drops are instilled in the user's test eye. The dye allows for easier viewing of the tear meniscus between the cornea and the tonometer tip 42, 142, and the anesthetic numbs the surface of the eye to ensure that the user does not feel any discomfort during testing.

Figure 9:
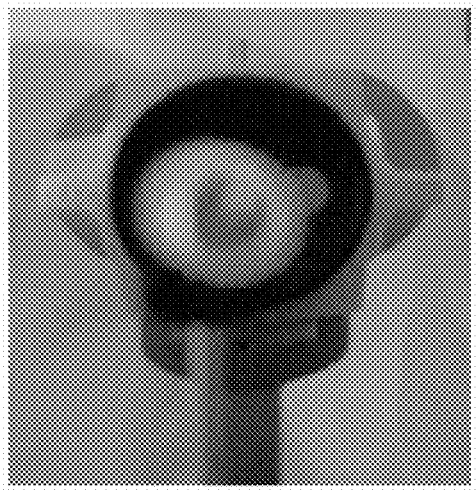
FIG. 9 is an exemplary video frame of the image seen by the user once the tonometer tip is aligned with the test eye.

When using apparatus 10, the user takes position in contact with chin-forehead rest 46, and moves the joystick 14 with one hand for course positioning to bring the tonometer tip 42 close to the test eye, aligning the tip 42 by looking directly at it such that it appear symmetric (see FIG. 9). Using the joystick 14, the user then brings the tonometer tip 42 into contact with his/her cornea. As the tonometer tip 42 applanates (flattens) the cornea of the test eye, the user views the applanation pattern (typically green in color) on one video monitor 28 with the observing eye. Next, the user manipulates the joystick 14 to adjust the tonometer tip 42 position to center the applanation pattern on the monitor 28. Finally, with the other hand, the user manipulates the tonometer dial 44 to obtain the applanation endpoint pattern for IOP measurement as described below. The user will then remove the tonometer tip 42 from the cornea using the joystick 14 and repeat the procedure on the other eye.

When using apparatus 110, a technician preferably sets the inter-pupillary distance of monitor 128 or display mirror 156 and tonometer tip 142 within apertures 154 for a particular user, where the components in ocular portions 150, 152 are arranged to track inwardly and outwardly together while remaining centered with respect to the longitudinal axis of housing 148. The technician also preferably sets the distance of the tonometer tip 142 to the cornea. The user holds apparatus 110 to her/his face, centers the tonometer tip 142 before the test eye, and then activates the positioning slide 190 with on/off button 162. Positioning slide 190 advances the tonometer tip 142 until it contacts the cornea with an initial applanating load, preferably 1 gram (10 mm Hg). The user then controls the applanating load with control lever 164 to reach the endpoint applanation pattern.

Figure 10:
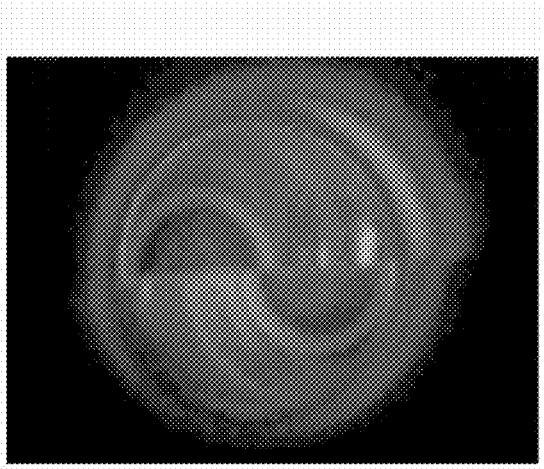
FIG. 10 is an exemplary video frame of the correct applanation endpoint pattern for self-measurement of IOP as seen by the user.
Figure 11:
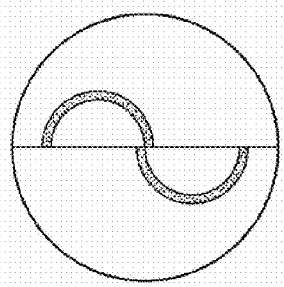
FIG. 11 is a schematic illustration of the correct applanation endpoint pattern for self-measurement of IOP.
Figure 12:
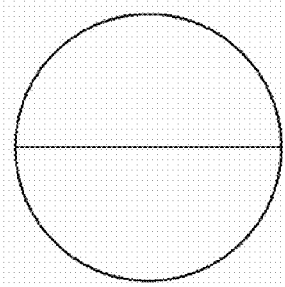
FIG. 12 is a schematic illustration of the case where no applanation pattern is observed.
Figure 13:
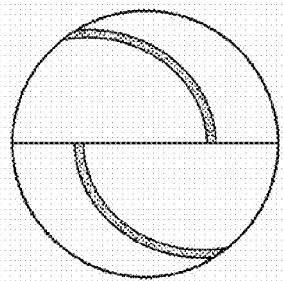
FIG. 13 is a schematic illustration of the applanation pattern observed if the apparatus is too close to the user's face.

If the user has aligned the tonometer tip 42, 142 to his/her eye, the user should see a pattern as shown in the exemplary video frame of FIG. 9. FIG. 10 shows an exemplary video frame of the correct applanation endpoint pattern for self-measurement of IP as seen by the user, while FIG. 11 is a schematic illustration of the same. As shown, the half circles are centered and are the same size, and the inner edges of the half circles just meet. If there is no pattern, the image will appear as in FIG. 12. The user should check to see that his/her head is placed firmly against the chin-forehead rest 46 or housing 148, and that the tonometer tip 42, 142 is in contact with his/her test eye. After adjustment, the applanation pattern should appear like that of FIG. 11. If the applanation pattern in FIG. 13 appears and does not change upon adjustment of the tonometer dial 44 or control lever 164, the apparatus 10, 110 is too close to the user's face. The user should withdraw his/her head from the apparatus 10, 110 and start the measurement over.

Figure 14:
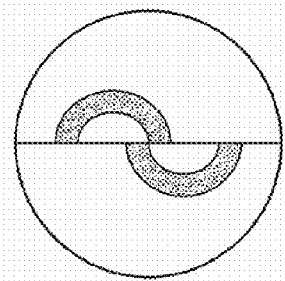
FIG. 14 is a schematic illustration of the applanation pattern observed when the fluorescein ring is too wide.
Figure 15:
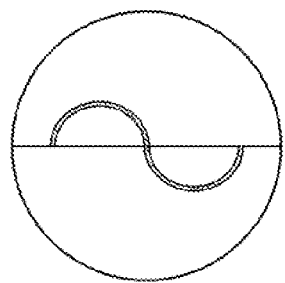
FIG. 15 is a schematic illustration of the applanation pattern observed when the fluorescein ring is too narrow.
Figure 16:
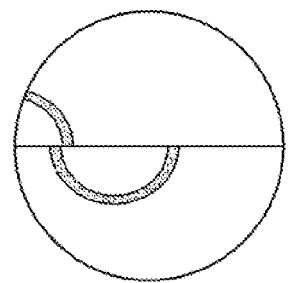
FIG. 16 is a schematic illustration of the applanation pattern observed when the tonometer tip is too far to the left on the test eye.
Figure 17:
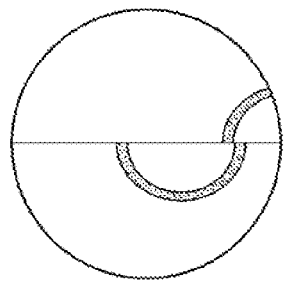
FIG. 17 is a schematic illustration of the applanation pattern observed when the tonometer tip is too far to the right on the test eye.
Figure 18:
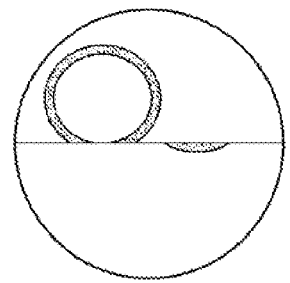
FIG. 18 is a schematic illustration of the applanation pattern observed when the tonometer tip is too high on the test eye.
Figure 19:
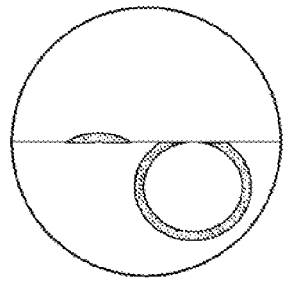
FIG. 19 is a schematic illustration of the applanation pattern observed when the tonometer tip is too low on the test eye.

In the applanation pattern illustrated in FIG. 14, the fluorescein ring is too wide. To correct this problem, the user should remove the tonometer tip 42, 142 from his/her test eye and lightly dab the tonometer tip 42, 142 with a cotton swab. In the applanation pattern shown in FIG. 15, the fluorescein ring is too narrow. Blinking the test eye a few times to spread the dye will correct this problem. In the applanation pattern depicted in FIG. 10, the tonometer tip 42, 142 is too far to the left on the test eye. The user should move the joystick 14 or adjust housing 148 to the right to bring the entire pattern into view. In the applanation pattern of FIG. 17, the tonometer tip 42, 142 is too far to the right on the test eye. The user should move the joystick 14 or adjust housing 148 to the left to bring the pattern fully into view. If the user sees the applanation pattern shown in FIG. 18, the tonometer tip 42, 142 is too high on the test eye. The user should turn the joystick 14 in a clockwise direction or adjust housing 148 downwardly to move the image down into view. If the user sees the applanation pattern of FIG. 19, the tonometer tip 42, 142 is too low on the test eye. The user should turn the joystick in a counter-clockwise direction or adjust housing 148 upwardly to move the pattern up into view.

Figure 20:
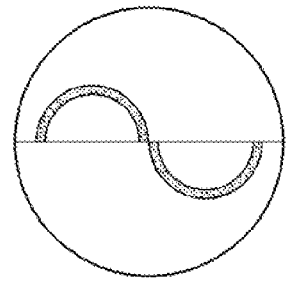
FIG. 20 is a schematic illustration of the applanation pattern observed when the pressure is too low.
Figure 21:
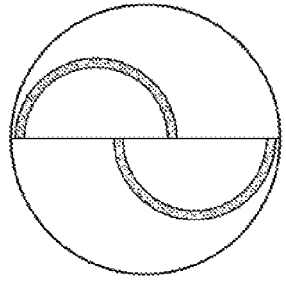
FIG. 21 is a schematic illustration of the applanation pattern observed when the pressure is too high.
Figure 22A:
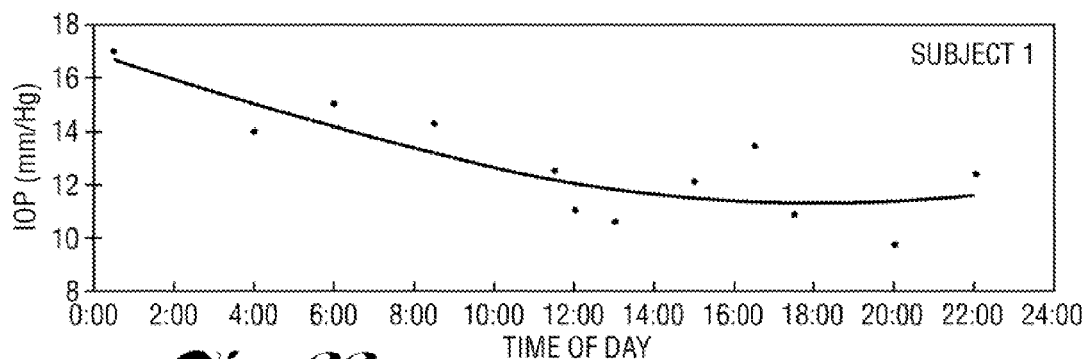
FIG. 22 are graphs of 24-hour home IOP self-measurements in four users obtained with the self-tonometry apparatus according to the present invention.
Figure 22B:
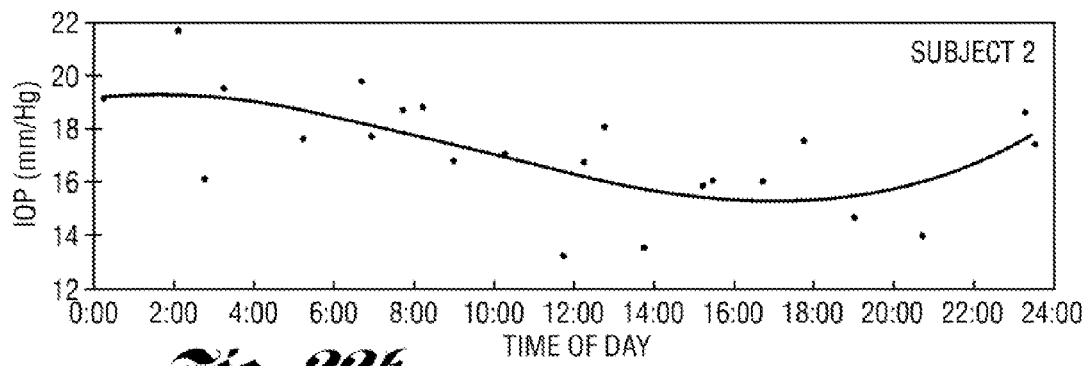
Figure 22C:
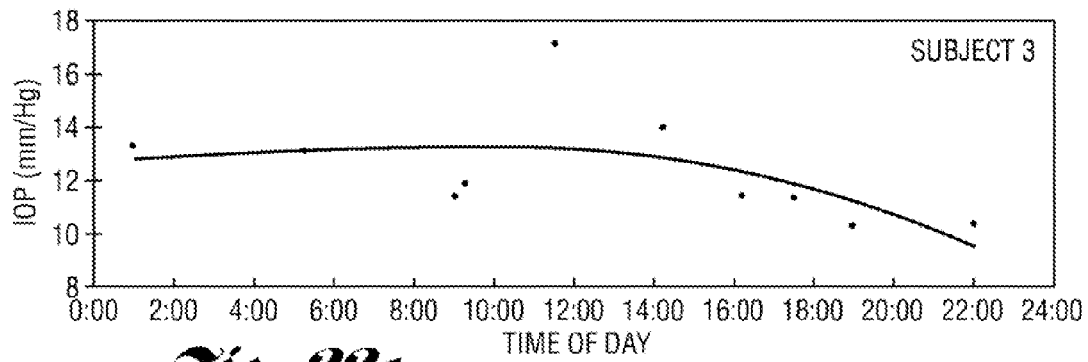
Figure 22B:
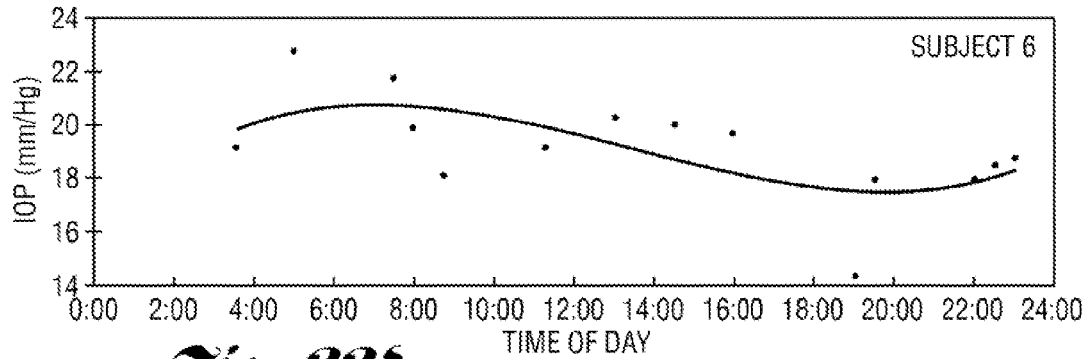

If the rings are not touching, as illustrated in FIG. 20, the pressure is too low. The user should turn the tonometer dial 44 towards himself or adjust control lever 164 to increase the pressure. After the pressure is increased, the applanation pattern should look like that of FIG. 11. If the rings are overlapping, as in FIG. 21, the pressure is too high. The user should turn the tonometer dial 44 away from himself or adjust control lever 164 to decrease the pressure. After the pressure is decreased, the applanation pattern should look like that of FIG. 11. Of course, the specific directional movement of the joystick 14, tonometer dial 44, control lever 164, and housing 148 described above is only exemplary.

To ensure that a user understands and is comfortable and confident in his/her operation of the self-tonometry apparatus 10, 110 of the present invention, an initial training session is preferably held with each user. This training session preferably includes the use of an instructional video and/or pamphlet that will guide the user through the basic manipulation of the apparatus 10, 110 for the range of applanation patterns they could observe. The training session can also include hands-on practice in obtaining the proper applanation pattern using a model eye (for example, Model TE-210, EyeTech, Morton Grove, Ill.), that will mount to the chin-forehead rest 46 or ocular portions 150, 152 of the apparatus 10, 110. This will serve as a simulator so that the user can become familiar with manipulation of the joystick 14, tonometer dial 44, housing 148, and control lever 164 to obtain the correct applanation endpoint pattern before measuring her/his IOP. Because the model eye can be set to particular pressures, it can also allow the technician/trainer to gauge the user's facility with the apparatus 10, 110. The preliminary estimate is that a trained user will be able to perform self-tonometry on both eyes using the apparatus 10, 110 of the present invention within three minutes.

The table below summarizes the experiments in five users in which each measured her/his IOP using apparatus 10 of the present invention and then had measurements made by an experienced measurer. Taking into account inter-observer variability and intra-observer measurement bias, measurements followed the protocol of AGIS (see Gordon et al., *Arch Ophthalmol* 1999, 117: 573-583; Anderson and Grant, *Invest Ophthalmol* 1973, 12: 204-212) and OHTS (see Gaasterland et al., *Am J Ophthalmol* 2000, 130: 429-440; Leonard et al., *Br J Ophthalmol,* 1983, 67: 362-366). Two consecutive self-measurements were taken, and if the measurements differed by 2 mm Hg or more, then a third measurement is taken. An experienced measurer, such as an ophthalmologist, then made two consecutive measurements using a standard slit lamp setup, again taking a third measurement if the first two differed by 2 mm Hg or more. Users were introduced to self-tonometry, but not trained, and their data were then acquired on another day. All measurements were made in a paired design (5 measurements per user, pairing the user's measurements with the experienced measurer's measurements), and measurements were made on the right eye only. For all users, the mean difference between self- and experienced measurements was within ~1.25 mm Hg. Further, the average standard deviation of differences (user minus experienced measurer) was 1.09. These data indicate that users can learn to effectively and accurately practice self-measurement of IOP using the self-tonometry apparatus 10, 110 of the present invention.

| User # | Age | Mean IOP Difference | Standard Deviation of Difference |
|---|---|---|---|
| 1 | 50 | −0.45 | 1.54 |
| 2 | 71 | 0.20 | 0.74 |
| 3 | 53 | −0.35 | 1.38 |
| 4 | 78 | −1.25 | 0.47 |
| 5 | 75 | 0.90 | 1.33 |
| MEAN = | | −0.19 | 1.09 |

FIG. 22 shows the results of an experiment wherein the self-tonometry apparatus 10 of the present invention was used by users to conduct 24-hour IOP self-measurement at home. Twenty-four hour self-tonometry by users 1, 2, and 3 from table 1 and a 61-year old ocular hypertensive user, subject 6. Using apparatus 10, users obtained self-tonometry data on their right eyes at random times during a 24 hour period. Each IOP point obtained at home was the mean of three consecutive readings for the eye. If a reading varied by more than 2.0 mm Hg, an additional reading was made. After a single instructional session, each user was easily able to obtain the correct applanation endpoint pattern on his/her test eye using the apparatus 10 of the present invention.

The apparatus and method according to the present invention provide a diagnostic tool that will enable opthalmologists to obtain a vastly increased volume of user IOP information throughout 24 hours. This could greatly improve medical control of IOP, the primary risk factor of glaucoma. The present invention also demonstrates the value of self-tonometry for studying the circadian rhythm of IOP. This could lead to the elucidation of the role of higher IOPs than have been measured clinically as a likely important factor in progression of the optic neuropathy of POAG and NTG, and in development of the neuropathy in patients with OHT.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An apparatus for the self-measurement of intraocular pressure by a user having a test eye and an observing eye, the apparatus comprising:
   a housing;
   a tonometer disposed within the housing and having a tonometer tip;
   an adjustment mechanism in communication with the tonometer for positioning the tonometer tip in contact with the test eye;
   an illuminator mounted within the housing adjacent the tonometer tip;
   a receiver aligned with the tonometer tip for receiving an applanation pattern created by contact of the tonometer tip with the test eye; and
   a display in communication with the receiver and oriented toward the user for displaying the applanation pattern to the observing eye,
   wherein the intraocular pressure of the test eye is determined from a force applied by the tonometer tip upon observation of a selected applanation pattern by the observing eye.

2. The apparatus according to claim 1, wherein the receiver includes a video camera, and the display includes at least one video monitor.

3. The apparatus according to claim 1, wherein the receiver includes a beam splitting mirror, and the display includes a display mirror aligned with the beam splitting mirror.

4. The apparatus according to claim 1, wherein the housing includes a base, a guide plate movably positionable with respect to the base, and a support extending upwardly from the guide plate, the support having the tonometer, receiver, and display mounted thereon.

5. The apparatus according to claim 4, further comprising a chin-forehead rest attached to the base.

6. The apparatus according to claim 4, further comprising a pair of lens holders mounted within the housing and arranged to receive corrective lenses therein.

7. The apparatus according to claim 1, wherein the housing is arranged to be hand-held and includes first and second ocular portions, wherein the tonometer tip and receiver are disposed within the first ocular portion, and the display is disposed within the second ocular portion.

8. The apparatus according to claim 1, further comprising a video recorder in communication with the receiver.

9. The apparatus according to claim 1, wherein the selected applanation pattern is an applanation endpoint pattern.

10. A hand-held apparatus for the self-measurement of intraocular pressure by a user having a test eye and an observing eye, the apparatus comprising:
a housing having a first ocular portion and a second ocular portion on one side thereof;
a tonometer disposed at least partially within the first ocular portion and having a tonometer tip;
an adjustment mechanism in communication with the tonometer for positioning the tonometer tip in contact with the test eye;
an illuminator mounted within the housing adjacent the tonometer tip;
a receiver disposed within the first ocular portion and aligned with the tonometer tip for receiving an applanation pattern created by contact of the tonometer tip with the test eye; and
a display disposed in the second ocular portion and in communication with the receiver for displaying the applanation pattern to the observing eye,
wherein the intraocular pressure of the test eye is determined from a force applied by the tonometer tip upon observation of a selected applanation pattern by the observing eye.

11. The apparatus according to claim 10, wherein the receiver includes a video camera, and the display includes at least one video monitor.

12. The apparatus according to claim 10, wherein the receiver includes a beam splitting mirror, and the display includes a display mirror aligned with the beam splitting mirror.

13. The apparatus according to claim 12, further comprising at least one focusing lens disposed within the housing and aligned with the display mirror for focusing the applanation pattern for the observing eye.

14. The apparatus according to claim 10, wherein the tonometer includes a force applicator for actuating movement of the tonometer tip to apply a force to the test eye, a strain gauge in communication with the force applicator for sensing an applied force, and a microprocessor in communication with the strain gauge for controlling the applied force and determining the intraocular pressure from the applied force.

15. The apparatus according to claim 10, wherein a first adjustment mechanism is provided on a top surface of the housing and a second adjustment mechanism is provided on a bottom surface of the housing such that the housing is operable in a first orientation and in a second orientation rotated 180° about its longitudinal axis, the housing including an aperture arranged to receive a member for activating one of the first and second adjustment mechanisms depending upon the orientation of the housing.

16. The apparatus according to claim 10, further comprising a plate including a first connector provided on a bottom surface thereof and the adjustment mechanism provided on a top surface thereof, wherein the housing includes a second connector on both a top and bottom surface thereof arranged to mate with the first connector such that the housing is operable in a first orientation and in a second orientation rotated 180° about its longitudinal axis.

17. The apparatus according to claim 10, further comprising an LCD display for displaying the intraocular pressure reading.

18. The apparatus according to claim 10, further comprising a video recorder in communication with the receiver.

19. The apparatus according to claim 10, wherein the selected applanation pattern is an applanation endpoint pattern.

20. A method for the self-measurement of intraocular pressure by a user, the method comprising:
providing a housing having a tonometer disposed therein, the tonometer having a tonometer tip;
placing a test eye and an observing eye of the user adjacent to the housing;
illuminating the test eye;
positioning the tonometer tip in contact with the test eye;
receiving an applanation pattern created by contact of the tonometer tip with the test eye;
displaying the applanation pattern to the observing eye; and
determining the intraocular pressure of the test eye based on the force applied by the tonometer tip upon observation of a selected applanation pattern by the observing eye.

21. The method according to claim 20, wherein the applanation pattern is received by a beam splitting mirror and displayed using a display mirror.

22. The method according to claim 20, wherein the applanation pattern is received with a video camera and displayed using at least one video monitor.

23. The method according to claim 20, further comprising instilling dye and anesthetic substances in the test eye.

24. The method according to claim 20, further comprising viewing the applanation pattern through corrective lenses.

25. The method according to claim 20, further comprising rotating the housing 180° about its longitudinal axis to obtain a measurement of intraocular pressure for another test eye.

26. The method according to claim 20, further comprising recording the applanation pattern with a video recorder.

27. The method according to claim 20, wherein determining the intraocular pressure includes observing an applanation endpoint pattern.

* * * * *